United States Patent
Luan

(10) Patent No.: US 10,150,943 B2
(45) Date of Patent: Dec. 11, 2018

(54) KLEBSIELLA SP. STRAIN AND METHOD FOR PREPARING MICROBIAL FLOCCULANT FROM SAME

(71) Applicant: QINGDAO YAODONG GROUP, Qingdao, Shandong (CN)

(72) Inventor: Xingshe Luan, Shandong (CN)

(73) Assignee: QINGDAO YAODONG GROUP, Shandong (CN)

( * ) Notice: Subject to any disclaimer, the term of this patent is extended or adjusted under 35 U.S.C. 154(b) by 302 days.

(21) Appl. No.: 15/184,973

(22) Filed: Jun. 16, 2016

(65) Prior Publication Data

US 2017/0101620 A1  Apr. 13, 2017

(30) Foreign Application Priority Data

Oct. 12, 2015 (CN) .......................... 2015 1 0656846

(51) Int. Cl.
*C12N 1/20* (2006.01)
*C12R 1/22* (2006.01)

(52) U.S. Cl.
CPC . *C12N 1/20* (2013.01); *C12R 1/22* (2013.01)

(58) Field of Classification Search
CPC .................................... C12N 1/20; C12R 1/22
See application file for complete search history.

(56) References Cited

U.S. PATENT DOCUMENTS 5,118,336 A  6/1992  Biez .................................. 71/6

FOREIGN PATENT DOCUMENTS

| CN | 1616358 A | 5/2005 |
|----|-----------|--------|
| CN | 102586331 A | 7/2012 |
| CN | 102876600 A | 1/2013 |
| CN | 103435250 A | 12/2013 |
| CN | 105176877 A | 12/2015 |

OTHER PUBLICATIONS

Huang, Jun et al., "Recent Investigation of Water Purification Microbial Flocculant" Journal of Shandong Normal University (Natural Science), vol. 23, No. 4, Dec. 2008, pp. 122-124.
Huang, Jun et al., "A Study of Optimum Fermentation Conditions of High Efficient Microbial Flocculant-Producing Stran DS16" Shandong Food Fermentation, No. 150, Mar. 2008, pp. 12-15.
Xing, Jie et al., "Identification of a Bioflocculant-Producing Strain and Its Removal Efficiency of 17 α-ethinylestradiol" China Water & Wastewater, vol. 29, No. 11, Jun. 2013, pp. 11-14.

*Primary Examiner* — Padmavathi Baskar
(74) *Attorney, Agent, or Firm* — J.C. Patents

(57) ABSTRACT

The example of the present invention discloses a *klebsiella* sp. strain and a method for preparing a microbial flocculant from the same. This strain is a *Klebsiella* sp. strain LDX1-1 which has been preserved in the China General Microbiological Culture Collection Center on Sep. 7, 2015, and the preservation number is CGMCC No. 11330. This strain can be used for preparing a microbial flocculate in an activated fermentation way.

8 Claims, No Drawings

Specification includes a Sequence Listing.

KLEBSIELLA SP. STRAIN AND METHOD FOR PREPARING MICROBIAL FLOCCULANT FROM SAME

CROSS-REFERENCE TO RELATED APPLICATION

This application claims the priority of Chinese Patent Application No. 201510656846.5, filed to the Chinese Patent Office on Oct. 12, 2015, titled "*KLEBSIELLA* SR. STRAIN AND METHOD FOR PREPARING MICROBIAL FLOCCULANTS FROM THE SAME", the entire contents of which are incorporated herein by reference.

TECHNICAL FIELD

The present invention relates to a *klebsiella* sp. strain and a method for preparing a microbial flocculant from the same, belonging to the field of biotechnology and bioengineering.

BACKGROUND OF THE PRESENT INVENTION

With the rapid industrial development, rapid population increase and other worldwide problems, water pollution is aggravated and water resource is in short. In recent years, 60 billion cubic meters of industrial wastewater and 20 billion cubic meters of domestic sewage are discharged each year in China. The seven major water systems, such as the Yangtze River and the Yellow River, are seriously polluted. The quality of water in ecological lakes and offshore regions is deteriorated to different extents. People's health and economic development are seriously threatened. The protection of water resource is highly urgent. China is one of the countries which are urgently lack of water, and its per-capita fresh water resource is only ¼ of the world average. Due to a large population and with the social development, the large amount of produced industrial wastewater and domestic swage seriously pollutes the limited water resource. Some phenomena of water shortage are shocking, and water resource has been at risk. *The Water Law of the People's Republic of China* established laws such as water resource protection, water conservation and efficient water use from the perspective of legislation. Water has become the scarcest resource.

For decades, during the sustainable utilization of water resource which maintains the human society, economic development and living environment, chemical flocculants play a significant role in purification of surface water and sewage treatment. However, by scientific research, it is increasingly found that chemical flocculants have chemical toxicity and contain hardly-degradable substance, and the residue and accumulation of chemical flocculants after being used and the migration and transformation thereof will cause serious harm to the human health, biodiversity interference and ecosystem balance.

Microbial flocculants are natural biological macromolecules produced by microorganisms, and are environmentally friendly products due to their properties of mild production conditions, non-toxic and harmless essence, high-efficiency, and environmental biodegradability. Microbial flocculants are novel biological water treatment agents, belonging to the modern novel fermentation products. The research on microbial flocculants has become the hot issue of the academic circles all over the world, and the science orientation has enabled microbial flocculants to be highly demanded. In the *Twelfth Five-Year Plan of Biological Industry Development* issued by the State Council in 2013, the industrialization and the popularization and application of novel fermentation products, and the development of high-performance environmentally friendly biological agents have already been taken as the key developing fields. However, in view of the research situation of microbial flocculants in the past 30 years, poor performance of spawn, costly production substrate, less-reasonable fermentation process, low product activity and similar problems still remain, resulting in low production output, high production cost and high product price. Consequently, the feasibility of specialization and the market acceptability are influenced.

For more than a decade, LUAN, Xingshe, the inventor of the present invention patent application, has been working on the research and development of microbial flocculants, and have achieved two patents: ZL200310105515.X and ZL201210010801.7. In ZL200310105515.X (inventor: LUAN, Xingshe; title: METHOD FOR PREPARING BIOFLOCCULANTS FROM *ARTHROBACTER*), the inventor selected *arthrobacter* for producing microbial flocculants by soil sampling. The metabolism of the selective culture medium for selecting this *arthrobacter* is highly targeted, and producing the culture medium of biological flocculants by fermentation with this *arthrobacter* is cheap. However, when producing microbial flocculants by fermentation with this selected strains, the yield is low ($\leq 42\%$) and the production output is also low ($\leq 0.9\%$). In ZL201210010801.7 (inventor: LUAN, Xingshe; title: METHOD FOR PREPARING BIOFLOCCULANTS BY HIGH-CONCENTRATION FERMENTATION), the inventor achieved higher production output ($\geq 2.0\%$) by fermentation in a bacterial quantity dominance way by separated *micrococcus* DS16. However, this method increases the equipment investment, and both the fermentation process and operation steps are slightly complex. Hence, for microbial flocculants which are green environmentally-friendly biological agents, making further improvements, maintaining the high efficiency, making the process more scientific and reasonable, increasing the production output and yield, and reducing the production and use cost are technical difficulties which must be overcome before the industrialization and the popularization and application.

SUMMARY OF THE PRESENT INVENTION

One example of the present invention provides a *Klebsiella* sp. strain LDX1-1 which is separated from moist soil below litters in the almond forest in the southern suburb of Jinan City, Shandong Province, China. This strain has been preserved in the China General Microbiological Culture Collection Center (CGMCC, address: Institute of Microbiology of Chinese Academy of Sciences, No. 3, Yard 1, Beichen Road West, Chaoyang District, Beijing, China) on Sep. 7, 2015, and the preservation number is CGMCC No. 11330.

Another example of the present invention further provides an application of the *Klebsiella* sp. strain LDX1-1 described above in preparing a microbial flocculant. The *Klebsiella* sp. strain LDX1-1 can be used for preparing a microbial flocculant.

Still another example of the present invention provides a method for preparing a microbial flocculant from the *Klebsiella* sp. strain LDX1-1 described above, specifically including:

(1) Liquid Spawn Culture activated slant spawn is inoculated into a liquid spawn culture medium, and then cultured while shaking at 150-180 r/min at 24-30° C. for 10-18 h to obtain a liquid spawn for later use; and the liquid spawn culture medium contains the following components in gram per liter: 10-15 g/L of sugar, 1.5-2.5 g/L of $NH_4NO_3$, 0.8-1.3 g/L of $K_2HPO_4$, 0.3-0.8 g/L of $MgSO_4$, 0.3-0.8 g/L of NaCl, and 0.01-0.04 g/L of $FeSO_4$; and (2) Fermentation the liquid spawn is inoculated into a fermentation medium in a volume ratio of 2-4% and then fermented in an activated fermentation way in a fermentation tank for 24-32 h to eventually obtain a fermentation broth at the end of fermentation, and the fermentation broth is filtered to remove impurities to eventually obtain a liquid protein polysaccharide (PPS) microbial flocculant; and by measurement of the fermentation broth, the yield of the microbial flocculant is higher than or equal to 60%, the production output thereof is higher than or equal to 2.0%, and the flocculation rate is higher than or equal to 94%.

The fermentation control conditions are as follows: temperature: 24-30° C.; air volume/culture volume/min: 0.25-0.8 VVM; and stirring speed: 200-600 r/min.

The fermentation medium contains the following components in gram per liter (g/L): 15-30 g/L of sugar, 1.5-4.5 g/L of $NH_4NO_3$, 0.8-2.0 g/L of $K_2HPO_4$, 0.2-0.7 g/L of $MgSO_4$, 0.2-0.8 g/L of NaCl, 0.01-0.04 g/L of $FeSO_4$, 0.01-0.05 g/L of $MnSO_4$, 0.1-0.4 g/L of extract of pine needles, 6-12 g/L of corn starch, 1-3 g/L of corn steep, and 0.018-0.040 g/L of $ZnSO_4$. The activator in this culture medium contains the following components: $MnSO_4$ and extract of pine needles.

The use of such a microbial flocculant is as follows: the microbial flocculant in a liquid state is directly mixed into the surface water, domestic sewage, industrial wastewater, water in ecological lakes, aquaculture wastewater, fermentation culture solution or the like.

A method for applying the microbial flocculant of the present invention to treat domestic sewage includes the following operations: adding a proper amount of microbial flocculant to domestic sewage inside a flocculation device having a stirring function, quickly mixing at a stirring speed of 120 r/min for 40 s and slowly mixing at a stirring speed of 60 r/min for 120 s, keeping the mixture standing for 30 min so that the pollutants are precipitated and separated, and collecting and measuring the supernatant. With regard to treatment of domestic sewage, the usage amount (dry weight) of the microbial flocculant PPS is 3-5 g per ton of water, the SS flocculation rate is higher than or equal to 90%, the COD removal rate is higher than or equal to 85%, the heavy metal $Mn^{2+}$ removal rate is higher than or equal to 85%.

DETAILED DESCRIPTION OF THE PRESENT INVENTION

Example 1: Screening of Strain (1) Sampling

Moist soil below litters in the almond forest in the southern suburb of Jinan City, Shandong Province, China was selected. The soil surface was scraped off by an aseptic sampling shovel. Soil at a height 3-10 cm below the earth surface was put into an aseptic bag on which the sampling date, time, place and vegetation were marked, and the soil strain sample was put into a refrigerator at 4° C. as soon as possible. Enrichment and screening of spawn were performed on that day or within two days.

(2) Screening

All components (except lysozyme) in the enrichment culture solution prescription were prepared to a liquid culture medium. The liquid culture medium was distributed with 50 mL in each 250 mL flask, subjected to high-pressure steam sterilization at 121° C. for 25 min, cooled to 25-28° C., added with a corresponding amount of lysozyme under aseptic conditions, and evenly mixed. The collected strain sample was inoculated into the prepared enrichment culture solution, well shaken, and cultured while shaking the flask at 120-180 r/min at 20-27° C. for 2-3 days to obtain an enrichment culture bacteria solution.

A selective culture medium was prepared, and a Φ9 cm plate was used as a selective culture medium plate. The enrichment culture bacteria solution was serially diluted, coated on the selective culture medium plate in a proper degree of dilution, and cultured at 20-27° C. for 2-3 days. Bacterial colonies having fast growth, high viscosity and light colored ring were selected. After purification, typical bacterial colonies were selected and inoculated into the slant culture medium, and stored in a refrigerator at 4° C. after being well cultured.

The culture media will be specifically described as below:

The enrichment culture solution contains the following components in gram per liter (g/L): 2 g/L of beef extract, 9 g/L of peptone, 5 g/L of NaCl, 0.6 g/L of $MgSO_4$, 0.03 g/L of lysozyme (0.5 million U/g), and 1000 mL of distilled water.

The selective culture medium contains the following components in gram per liter (g/L): 25 g/L of glycerol, 2.5 g/L of $NaNO_3$, 1.2 g/L of $K_2HPO_4$, 0.4 g/L of $MgSO_4$, 0.4 g/L of NaCl, 0.015 g/L of $FeSO_4$, 2.0 g/L of $CuSO_4$, 2.0 g/L of sodium propionate, and 15 g/L of purified agar powder.

The slant culture medium contains the following components in gram per liter (g/L): 12 g/L of glycerol, 2.5 g/L of $NaNO_3$, 0.9 g/L of $K_2HPO_4$, 0.6 g/L of $MgSO_4$, 0.6 g/L of NaCl, 0.015 g/L of $FeSO_4$, and 14 g/L of purified agar powder.

(3) Identification of Strain

The screened strain had the following individual morphological characteristics: long rod: 1.5~1.8 μm×2.5~5.0 μm, and short rod: 1.5~1.8 μm×1.8~2.5 μm; arrayed in a single one; with rich slime layer; no motion; no spore; and being aerobic.

The screened strain had the following culture characteristics: opaque bacterial colonies which were protruded in the center, tidy in the margin, glossy and high in viscosity were produced on the beef extract and peptone culture medium plate; and bacterial lawns which were thick, glossy, high in viscosity and faint yellow were produced on the slant surface. The screened strain had the following physiological and biochemical characteristics: the catalase test was positive; in the peptone water culture medium, glucose, cane sugar, maltose and arabinose can be highly fermented to produce acid and gas, fructose, xylose, glycerol and lactose can be fermented to produce acid and gas, dextrin and starch can be slowly fermented to produce acid and gas, and xylitol cannot be fermented to produce acid and gas; the methyl red was negative and V-P was positive; it was resistant against 7% NaCl growth; Φ17 cm bulky bacterial colonies were formed on the starch hydrolysis plate after 2 days; the oil hydrolysis was negative; the gelatin hydrolysis was negative; the litmus milk was reduced; and the urease was positive.

The following is the measurement result of the 16SrDNA sequence of this train (SEQ-1):

ACGCTGGCGGCAGGCCTAACACATGCAAGTCGAGCGGTAGCACAGAGAGC

TTGCTCTCGGGTGACGAGCGGCGGACGGGTGAGTAATGTCTGGGAAACTG

CCTGATGGAGGGGGATAACTACTGGAAACGGTAGCTAATACCGCATAACG

TCGCAAGACCAAAGTGGGGGACCTTCGGGCCTCATGCCATCAGATGTGCC

CAGATGGGATTAGCTAGTAGGTGGGGTAATGGCTCACCTAGGCGACGATC

CCTAGCTGGTCTGAGAGGATGACCAGCCACACTGGAACTGAGACACGGTC

CAGACTCCTACGGGAGGCAGCAGTGGGGAATATTGCACAATGGGCGCAAG

CCTGATGCAGCCATGCCGCGTGTGTGAAGAAGGCCTTCGGGTTGTAAAGC

ACTTTCAGCGGGGAGGAAGGCGTTGAGGTTAATAACCTTGTCGATTGACG

TTACCCGCAGAAGAAGCACCGGCTAACTCCGTGCCAGCAGCCGCGGTAAT

ACGGAGGGTGCAAGCGTTAATCGGAATTACTGGGCGTAAAGCGCACGCAG

GCGGTCTGTCAAGTCGGATGTGAAATCCCCGGGCTCAACCTGGGAACTGC

ATTCGAAACTGGCAGGCTA.

This strain is named *Klebsiella* sp. strain LDX1-1 which has been preserved in the China General Microbiological Culture Collection Center (CGMCC, address: Institute of Microbiology of Chinese Academy of Sciences, No. 3, Yard 1, Beichen Road West, Chaoyang District, Beijing, China) on Sep. 7, 2015, and the preservation number is CGMCC No. 11330.

Example 2

The liquid spawn culture medium contains the following components in gram per liter: 12 g/L of sugar, 2 g/L of $NH_4NO_3$, 0.8 g/L of $K_2HPO_4$, 0.5 g/L of $MgSO_4$, 0.4 g/L of NaCl, and 0.013 g/L of $FeSO_4$.

The fermentation culture medium contains the following components in gram per liter (g/L): 23 g/L of sugar, 2 g/L of $NH_4NO_3$, 1.2 g/L of $K_2HPO_4$, 0.5 g/L of $MgSO_4$, 0.4 g/L of NaCl, 0.015 g/L of $FeSO_4$, 0.02 g/L of $MnSO_4$, 0.2 g/L of extract of pine needles (manufactured by Xi'an RunXue Bio-technology Co. Ltd., with an extraction proportion of 10:1), 7 g/L of corn starch, 1.8 g/L of corn steep, and 0.03 g/L of $ZnSO_4$.

(1) Liquid Spawn Culture

Activated slant spawn was inoculated into a liquid spawn culture medium, and then cultured while shaking at 170 r/min at 26° C. for 13 h to obtain a liquid spawn for later use; and (2) Fermentation the liquid spawn was inoculated into a fermentation medium in a volume ratio of 2.5% and then fermented in an activated fermentation way in a fermentation tank for 30 h (the fermentation control conditions were as follows: temperature: 26° C.; air volume/culture volume/min: 0.45 VVM; and stirring speed: 500 r/min) to eventually obtain a fermentation broth at the end of fermentation, and the fermentation broth was filtered to remove impurities to eventually obtain a liquid protein polysaccharide (PPS) microbial flocculant; and by measurement of the fermentation broth, the yield of the microbial flocculant was 61%, the production output thereof was 2.1%, and the flocculation rate was 95%.

The yield of the microbial flocculant was measured by the following method: the pH of the microbial flocculant was adjusted to 7.0; the microbial flocculant was mixed with two and a half-fold amount of absolute ethanol for precipitation and centrifuged at 5000 r/min for 5 min to obtain the primary precipitate; the primary precipitate was washed with six-fold amount of absolute ethanol, and centrifuged at 5000 r/min for 5 min to obtain the secondary precipitate; the secondary precipitate was dried in vacuum at 40° C. for 6 h, and the dry weight thereof was obtained. Yield=(dry weight of the flocculant (Kg)/dry weight of carbon source (Kg))×100%.

The flocculation rate was measured by the following method: 0.4% (by weight) of kaolin clay suspension and 5% (by weight) of $CaCl_2$ solution were prepared; 98% (by volume) of kaolin clay suspension and 2% (by volume) of $CaCl_2$ solution were added to a reaction cup of a six-motor stirrer, and evenly mixed to form a flocculation system for later use. During the measurement, 20 μL of fermentation broth was added to every 100 mL of flocculation system, quickly mixed at a stirring speed of 120 r/min for 40 s and then slowly mixed at a stirring speed of 60 r/min for 120 s, and kept standing for 5 min; the supernatant was collected; and an OD value B at a wavelength of 550 nm was obtained; instead of fermentation broth, distilled water was added and the above operations were operated to obtain an OD value A.

Flocculation rate=$\{(A-B)/A\}\times 100\%$.

Example 3: Application of the Microbial Flocculant in Treatment of Sewage

The microbial flocculant prepared in Example 2 was applied to the treatment of domestic sewage. A method for treating domestic sewage includes the following operations: adding a proper amount of microbial flocculant to domestic sewage inside a flocculation device having a stirring function, quickly mixing at a stirring speed of 120 r/min for 40 s and slowly mixing at a stirring speed of 60 r/min for 120 s, keeping the mixture standing for 30 min so that the pollutants were precipitated and separated, and collecting and measuring the supernatant.

The treatment of domestic sewage (the chemical oxygen demand (COD): 859 mg/L; the total amount of phosphorus: 22.9 mg/L; the amount of $Mn^{2+}$:0.434 mg/L; and the amount of $Fe^{3+}$: 84.6 mg/L) from Qingdao City Investment Daren Water Supply Co., Ltd., with the usage amount (dry weight) of the PPS microbial flocculant of 3-5 g per ton of water, showed the following excellent results: the flocculation rate of suspended solids (SS) was 93%; the COD removal rate was 93%; the total phosphorus removal rate was 86%; the heavy metal $Mn^{2+}$ removal rate was 87%; and the $Fe^{3+}$ removal rate was 97%.

The examples of the present invention has the following technical effects: a high-activity microbial flocculant producing strain is selected, i.e., *Klebsiella* sp. strain LDX1-1, and producing a microbial flocculant with this strain in a high yield in an activated fermentation way has the advantages of quick growth of the strain, high metabolic capacity (yield≥60%), short fermentation cycle (≤32 h), high production output (≥2.0%), high flocculation rate (≥94%) and the like. When the microbial flocculant prepared in the present invention is applied to treatment of domestic sewage, the SS flocculation rate is higher than or equal to 90%, the COD removal rate is higher than or equal to 85%, the heavy metal $Mn^{2+}$ removal rate is higher than or equal to 85%. Such a microbial flocculant has board development prospect and good application value.

What is claimed is:

1. A *Klebsiella* sp. strain LDX1-1, the preservation number of which is CGMCC No. 11330.

2. Application of the *Klebsiella* sp. strain LDX1-1 of claim 1 in preparing a microbial flocculant.

3. A method for preparing a microbial flocculant from the *Klebsiella* sp. strain LDX1-1 of claim 1, the method comprises:

(1) liquid spawn culture activated slant spawn is inoculated into a liquid spawn culture medium, and then cultured while shaking at 150-180 r/min at 24-30° C. for 10-18 h to obtain a liquid spawn for later use; and the liquid spawn culture medium contains the following components in gram per liter: 10-15 g/L of sugar, 1.5-2.5 g/L of $NH_4NO_3$, 0.8-1.3 g/L of $K_2HPO_4$, 0.3-0.8 g/L of $MgSO_4$, 0.3-0.8 g/L of NaCl, and 0.01-0.04 g/L of $FeSO_4$; and (2) fermentation the liquid spawn is inoculated into a fermentation medium in a volume ratio of 2-4% and then fermented in a fermentation tank for 24-32 h to eventually obtain a fermentation broth at the end of fermentation, and the fermentation broth is filtered to remove impurities to eventually obtain a microbial flocculant; and the fermentation medium contains the following components in gram per liter: 15-30 g/L of sugar, 1.5-4.5 g/L of $NH_4NO_3$, 0.8-2.0 g/L of $K_2HPO_4$, 0.2-0.7 g/L of $MgSO_4$, 0.2-0.8 g/L of NaCl, 0.01-0.04 g/L of $FeSO_4$, 0.01-0.05 g/L of $MnSO_4$, 0.1-0.4 g/L of extract of pine needles, 6-12 g/L of corn starch, 1-3 g/L of corn steep, and 0.018-0.040 g/L of $ZnSO_4$.

4. The method for preparing a microbial flocculant according to claim 3, wherein the fermentation control conditions in the step (2) are as follows: temperature: 24-30° C.; air volume/culture volume/min: 0.25-0.8 VVM; and stirring speed: 200-600 r/min.

5. The method for preparing a microbial flocculant according to claim 3, wherein the liquid spawn culture medium contains the following components in gram per liter: 12 g/L of sugar, 2 g/L of $NH_4NO_3$, 0.8 g/L of $K_2HPO_4$, 0.5 g/L of $MgSO_4$, 0.4 g/L of NaCl, and 0.013 g/L of $FeSO_4$.

6. The method for preparing a microbial flocculant according to claim 3, wherein the fermentation medium contains the following components in gram per liter: 23 g/L of sugar, 2 g/L of $NH_4NO_3$, 1.2 g/L of $K_2HPO_4$, 0.5 g/L of $MgSO_4$, 0.4 g/L of NaCl, 0.015 g/L of $FeSO_4$, 0.02 g/L of $MnSO_4$, 0.2 g/L of extract of pine needles, 7 g/L of corn starch, 1.8 g/L of corn steep, and 0.03 g/L of $ZnSO_4$.

7. The method for preparing a microbial flocculant according to claim 4, wherein the liquid spawn culture medium contains the following components in gram per liter: 12 g/L of sugar, 2 g/L of $NH_4NO_3$, 0.8 g/L of $K_2HPO_4$, 0.5 g/L of $MgSO_4$, 0.4 g/L of NaCl, and 0.013 g/L of $FeSO_4$.

8. The method for preparing a microbial flocculant according to claim 4, wherein the fermentation medium contains the following components in gram per liter: 23 g/L of sugar, 2 g/L of $NH_4NO_3$, 1.2 g/L of $K_2HPO_4$, 0.5 g/L of $MgSO_4$, 0.4 g/L of NaCl, 0.015 g/L of $FeSO_4$, 0.02 g/L of $MnSO_4$, 0.2 g/L of extract of pine needles, 7 g/L of corn starch, 1.8 g/L of corn steep, and 0.03 g/L of $ZnSO_4$.

* * * * *

SEQUENCE LISTING

<160> NUMBER OF SEQ ID NOS: 1

<210> SEQ ID NO 1
<211> LENGTH: 619
<212> TYPE: DNA
<213> ORGANISM: Klebsiella sp.

<400> SEQUENCE: 1

```
acgctggcgg caggcctaac acatgcaagt cgagcggtag cacagagagc ttgctctcgg      60
gtgacgagcg gcggacgggt gagtaatgtc tgggaaactg cctgatggag ggggataact     120
actggaaacg gtagctaata ccgcataacg tcgcaagacc aaagtggggg accttcgggc     180
ctcatgccat cagatgtgcc cagatgggat tagctagtag gtggggtaat ggctcaccta     240
ggcgacgatc cctagctggt ctgagaggat gaccagccac actggaactg agacacggtc     300
cagactccta cgggaggcag cagtggggaa tattgcacaa tgggcgcaag cctgatgcag     360
ccatgccgcg tgtgtgaaga aggccttcgg gttgtaaagc actttcagcg gggaggaagg     420
cgttgaggtt aataaccttg tcgattgacg ttacccgcag aagaagcacc ggctaactcc     480
gtgccagcag ccgcggtaat acggagggtg caagcgttaa tcggaattac tgggcgtaaa     540
gcgcacgcag gcggtctgtc aagtcggatg tgaaatcccc gggctcaacc tgggaactgc     600
attcgaaact ggcaggcta                                                   619
```